(12) United States Patent
Chelle et al.

(10) Patent No.: US 12,179,400 B2
(45) Date of Patent: Dec. 31, 2024

(54) MULTIPLE-MATRIX MONOLITHIC MOULDED PART FOR THE DIFFUSION OF ACTIVE INGREDIENTS AND METHOD FOR OBTAINING SAME

(71) Applicant: AB7 Innovation S.A.S.U., Deyme (FR)

(72) Inventors: René Chelle, Deyme (FR); Arnaud Vilbert, Baziege (FR); Sophie Leclerc, Toulouse (FR)

( * ) Notice: Subject to any disclaimer, the term of this patent is extended or adjusted under 35 U.S.C. 154(b) by 431 days.

(21) Appl. No.: 16/643,278

(22) PCT Filed: Aug. 24, 2018

(86) PCT No.: PCT/FR2018/000208
§ 371 (c)(1),
(2) Date: Feb. 28, 2020

(87) PCT Pub. No.: WO2019/043303
PCT Pub. Date: Mar. 7, 2019

(65) Prior Publication Data
US 2020/0206994 A1    Jul. 2, 2020

(30) Foreign Application Priority Data
Sep. 1, 2017   (FR) ...................... 1770912

(51) Int. Cl.
| B29C 45/16 | (2006.01) |
| A01N 25/10 | (2006.01) |
| A01N 25/24 | (2006.01) |
| A01N 25/34 | (2006.01) |
| A61L 9/04 | (2006.01) |
| A61L 9/12 | (2006.01) |
| B29K 105/00 | (2006.01) |

(52) U.S. Cl.
CPC .............. *B29C 45/16* (2013.01); *A01N 25/10* (2013.01); *A01N 25/24* (2013.01); *A01N 25/34* (2013.01); *A61L 9/042* (2013.01); *A61L 9/12* (2013.01); *B29K 2105/0011* (2013.01); *B29K 2105/0029* (2013.01); *B29K 2105/0035* (2013.01)

(58) Field of Classification Search
CPC ........ B29C 45/16; A01N 25/10; A01N 25/24; A61L 9/042; B29K 2105/0011; B29K 2105/0029; B29K 2105/0035
See application file for complete search history.

(56) References Cited

U.S. PATENT DOCUMENTS

| 5,248,700 A | 9/1993 | Lance |
| 2003/0075833 A1 | 4/2003 | Thomson |
| 2011/0108632 A1 | 5/2011 | Brandenburg et al. |
| 2013/0251773 A1* | 9/2013 | Galiatsatos ............ A01N 25/34 424/409 |

FOREIGN PATENT DOCUMENTS

| DE | 102004015784 A1 * | 10/2005 | ............. A01N 25/10 |
| EP | 0178908 | 7/1991 | |
| EP | 0539295 | 3/1995 | |
| EP | 1064935 | 1/2001 | |
| EP | 1100669 | 5/2001 | |
| EP | 2064046 | 12/2009 | |
| EP | 1620060 | 3/2010 | |
| EP | 2858687 | 3/2017 | |
| FR | 2533412 | 3/1984 | |
| FR | 2905299 | 3/2008 | |
| JP | 3240088 | 12/2001 | |
| WO | 2013184251 | 12/2013 | |

* cited by examiner

*Primary Examiner* — Snigdha Maewall
(74) *Attorney, Agent, or Firm* — Benoît & Côté, Inc.

(57) ABSTRACT

This invention relates to a monolithic molded part comprising multiple cohesive matrices for the simultaneous diffusion of volatile active ingredients, in contact or separately, wherein said multiple matrix is formed by the combination of several simple matrices, characterized in that each of said simple matrices is capable of containing one or more active ingredient(s), each active ingredient having its own release kinetics.

19 Claims, 2 Drawing Sheets

Figure 1:
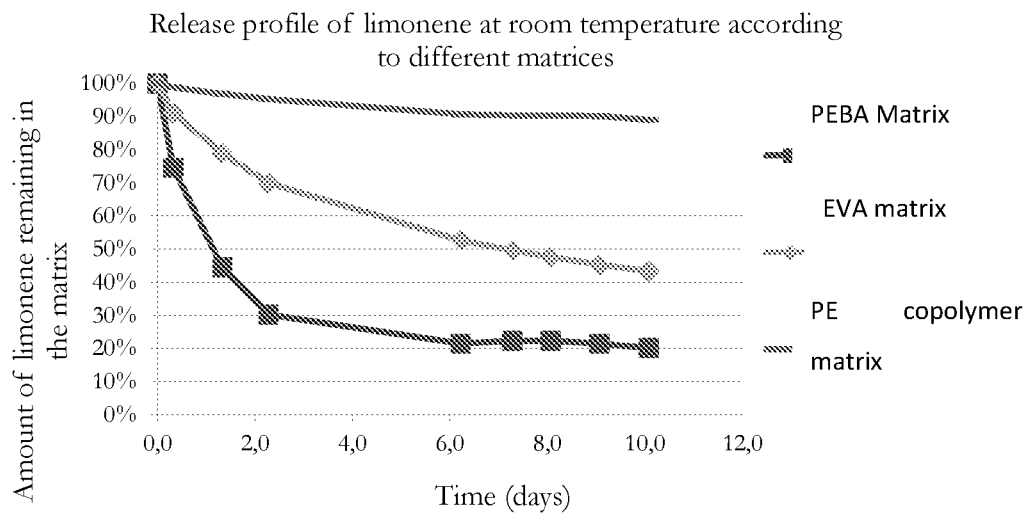

MULTIPLE-MATRIX MONOLITHIC MOULDED PART FOR THE DIFFUSION OF ACTIVE INGREDIENTS AND METHOD FOR OBTAINING SAME

This invention relates to diffusion devices comprising at least two different active ingredients and their manufacturing process. In particular, this invention relates to a monolithic molded part made of a polymer matrix comprising at least two different active ingredients, each of which has its own release kinetics, which kinetics it is desired to control, in order to obtain a desired effect on an intended target.

In the treatment of insect pests such as ectoparasites (ticks and fleas), it is necessary to simultaneously diffuse a mixture of several active ingredients so as to cover a wide spectrum of action against said pests. Often, the active ingredients are incorporated in a single carrier, which can be solid in the form of a polymer matrix (collars, bracelets, patches, etc.), semi-solid (gels, creams, etc.) or liquid (sprays, lotions, etc.). However, it is known to those skilled in the art that the nature of the macromolecular matrices and/or that of the solvent significantly influence the kinetics of diffusion of the active ingredients incorporated into these carriers.

Conversely, the behavior of the active agents, determined by their physico-chemical characteristics and their affinity with respect to a matrix and the environment external to it, can also be completely different. Indeed, it can happen that when two different active ingredients are incorporated into a single matrix, they behave differently in terms of release in the sense that one is easily released while the other is firmly sequestered in the matrix.

In the case of solid polymer matrix carriers, in particular of antiparasitic devices comprising an insecticide and a skin protection agent, collars are known from patent FR2533412 that are constituted of two strips, joined laterally, to form a mixed, double strip made of a polyvinyl chloride (PVC) homopolymer, wherein one of the two strips contains a synthetic insecticidal substance (pyrethroids, organohalogens, carbamates and formamidines), while the other strip contains a fatty acid having from $C_{10}$ to $C_{20}$, the role of which is to avoid skin manifestations, caused by insecticide, in animals. The collar is obtained from two mixtures of powders extruded in two different extruders connected at the outlet by a single die head. The objective of this patent is to obtain a regular and identical diffusion of the insecticide and the fatty acid used to protect the skin; regular diffusion should be understood as being diffusion rates of the two substances that are as close as possible to one another, if not substantially identical. Furthermore, the result is considered optimal when the diffusion rates of each of the two substances are close to one another.

Likewise, patent EP0178908 describes an antiparasitic collar for animals consisting of a first matrix comprising at least one insecticide prone to irritate the skin, wherein said first matrix is co-extruded with a second plastic matrix, also comprising an insecticide, and wherein at least part of the second matrix is between the skin of the animal and the first matrix. This patent is intended to provide a pest control collar that is non-irritating to the skin of animals. The plastic includes polyvinyl chloride (PVC), ethylene vinyl acetate (EVA) copolymers, vinyl acetal copolymers, vinyl alcohol copolymers, vinylbenzene copolymers and vinyldiene chlorides. The insecticides are pyrethroids, carbamates and organophosphates.

In U.S. Pat. No. 5,248,700, a polymer matrix system is disclosed in which different active ingredients can be incorporated simultaneously at different concentrations. To do this, the active material is first incorporated into a microporous polymer powder to constitute the active ingredient, then said active ingredient is dispersed within a biodegradable polymer.

International patent application WO9320693 discloses a system intended for treatment of tick infestations in humans. The system is a strip made up of a core of thermoplastic polymer material (polyethylenes, polypropylenes, polyamides, polycarbonates) loaded with high-concentration insecticide wrapped in a textile material serving as a physical barrier between the insecticide and the skin.

Patent EP0539295 discloses molded systems for the distribution of antiparasitic active agents in which, on the one hand, a considerable quantity of these active ingredients is not released and is unavailable for use against the target pests, this thus reducing the cost-efficiency and the useful life of these products and, on the other hand, in which the release of the active ingredients does not take place at a constant speed. This patent therefore proposes a solid PVC matrix loaded with antiparasitic active ingredient comprising a very large quantity of liquid plasticizer and miscible with PVC so that the PVC/plasticizer/active ingredient mixture remains fluid and dry, in order to facilitate the release of the active ingredient from said solid matrix.

In complete contrast, in order to regulate the diffusion of a scent of a perfume within a multi-injected molded carrier, Patent EP2064046 discloses an injected part diffusing scents, wherein this part is produced of at least two different polymers, obtained by simultaneous or sequential injection; the first polymer constitutes a skin, wrapping a core, which contains a perfume, while said core is formed by the second polymer. In order to regulate the diffusion of the perfume, mineral fillers incorporated into the skin are specified. Likewise, patent EP2858687 discloses a deodorizing article consisting of a core made of a first thermoplastic polymer overmolded by injection by a sleeve in another perfumed polymer.

Patent EP1620060 discloses a ring comprising unitary segments wherein each segment, obtained by simultaneous injection, is made of a thermoplastic polymer containing a drug; wherein the ends of the unit segments are linked together by means of an adhesive.

Patent EP1064935 discloses an ingestible pharmaceutical composition obtained, in particular, by co-injection of a mixture consisting of polymethacrylates and of drugs; the mass ratio of polyacrylates within the mixture influences the modularity of drug release. Said composition has a concentric structure in that it consists of a core and a wrapping.

Patent application US2011/0108632 discloses a fragrance diffuser clip obtained by bi-injection, consisting of a central part overmolded by a wrapping.

Patent JP3240088 discloses a housing, in two parts, with a concentric structure, made of thermoplastic resin. Each of the parts has a core wrapped, by overmolding, by a rigid resin devoid of active material. The control of the release of the active materials is carried out in particular by means of the grooves made on the wrapping.

The injected parts described above, the structure of which is concentric, can have drawbacks, in particular in terms of regulating the diffusion of the active material when the latter is incorporated into the core, but also in terms of continuity, due to overmolding of the structure of the final device.

It is therefore desirable to provide a molded part consisting of at least two simple matrices, having a non-concentric continuous structure, loaded with at least two different active materials. It follows that, during use, each of the matrices spontaneously releases the active material which it contains, at its own speed, depending on its formulation.

Likewise, it is also desirable to completely empty at least one simple matrix of the active material which it contains, which makes it possible to have full availability of said active material, and thus to avoid waste while making the part more environmentally friendly after use. Indeed, over time, as the molded part is used, it tends towards equilibrium, so that partial pressure in one of the simple, overplasticized matrices decreases since the quantity of solvent therein is greater than that of the neighboring matrix. In fact, the solvent of the over-plasticized matrix migrates to the neighboring under-plasticized matrix, which has the effect of emptying this afore-mentioned matrix of its active material.

Consequently, the molded part according to this invention comprises at least two simple matrices, each being loaded with a different active material, the single matrices being welded side to side or face to face, so that the side to side or face to face junctions of two neighboring matrices penetrate into each other, by partial fusion of the polymer which constitutes them, which allows movement of the active material solvent from one simple matrix to another. Such migration can only be obtained when, on the one hand, the polymers are compatible with one another, in particular due to the fact that they belong to the same chemical family and, on the other hand, the simple matrices are molded simultaneously by multi-shot molding.

Generally speaking, in the framework of antiparasitic treatment of animals by means of the synergistic combination of two active ingredients in a single polymer matrix, there are situations in which it is necessary for one of the active ingredients to have a faster speed than the other to achieve the desired efficacy. Conversely, the case may also arise in which the speed of simultaneous diffusion of the two active materials must be identical, or very close to one another, in order to achieve the intended insecticidal efficacy.

On reading the above state of the art, the mixtures of active ingredients, in particular insecticides or perfumes, are incorporated into single solid matrices made of a single type of thermoplastic polymer. It is deduced from these approaches that the insecticides or the perfumes are solubilized together in a single solvent before being incorporated into a single type of polymer. Obviously, the above-mentioned approaches would not be suitable when at least two active ingredients, different by their physicochemical nature, are present, solubilized by a single solvent, then incorporated into a single matrix of thermoplastic polymer. It follows that these approaches do not constitute a lever for action for controlling, in isolation, the specific kinetics of each of said active ingredients. Consequently, it is not possible to control the release kinetics of at least two active ingredients in terms of modularity, particularly when this modularity is necessary to induce and/or optimize the effect of each of the active ingredients on a target. The target can be made up of harmful insects, a defined environment or even the skin; in any event, the target depends on the nature of the active ingredient released.

Furthermore, it is clear that the prior art does not disclose any system for diffusing active ingredients which allows compatibilization, either:
of antagonistic activities, namely active ingredients which must be released simultaneously but with different kinetics, or else by the risk that they will react with each other, if they were mixed in a single matrix which distorts the desired effect, or even by the fact that at least one active ingredient slows down the release of at least one other,
of complementary activities, namely by obtaining release kinetics, staggered over time of the active ingredients (example: active ingredient A is released before active ingredient B, etc.), or with a different release time or with active ingredients that are different but complementary in their action, which makes it possible, for example, to obtain a shock effect which precedes a treatment effect, or else to obtain the release of several active ingredients, each of which induces a different effect for the benefit of the treatment of a human or animal subject.

Likewise, the prior art in no way seeks or suggests the provision of a monolithic diffusing carrier made of a polymer matrix loaded with at least two different active ingredients, each having its own release kinetics, wherein it is necessary to obtain the desired effect that the two active ingredients are released simultaneously, at a substantially identical or different rate of speed over time. Furthermore, there is no description therein of a monolithic molded part made of a polymer matrix made up of the association of at least two polymer matrices, other than PVC, one of which comprises an insecticide from the family of pyrethroids or its derivatives and the other, an active ingredient other than pyrethroids; wherein the rate of diffusion of the two active ingredients is close to one another, in order to effectively produce, over a long time, the anti-insect effect, in a human or animal subject.

In general, the intended beneficial effects, within the meaning of the invention, include, in a non-exhaustive manner, biocidal effects, in particular insecticide, repellent and attractive effects, perfuming and deodorant effects, cosmetic care, soothing effects, all the way to treatments by the delivery of pharmaceutical or phytosanitary substances.

It is known that the technique of shaping polymers by multi-shot molding makes it possible to obtain a molded part, that is complex in its structure, making it possible to combine the complementary properties of polymers that are compatible with each other or that have been made compatible. The Applicant has diverted this technique, normally dedicated to the design of composite mechanical devices, to the development of a molded monolithic diffusion piece with multiple effects, managed separately.

Consequently, the first object of this invention is a monolithic molded part made up of multiple cohesive matrices, having a non-concentric continuous structure, made up of the combination of two to four simple matrices, welded together and obtained using multi-shot molding, wherein each of said simple matrices is made of thermoplastic polymer and contains at least one active ingredient, each of which has its own release kinetics, and that the whole of said active ingredients are released simultaneously at substantially different or substantially similar speeds so that the sum of the quantities of active ingredients released makes it possible to achieve the desired beneficial effects by synergy, characterized in that the neighboring simple matrices are welded together, side by side or face to face, so that the weld ensures the structural continuity of the part and, in which said weld, which constitutes the interface between the neighboring matrices, is constituted by the mixture, in the molten state, of polymer(s) forming one and the other of said neighboring matrices. Structural continuity is adapted to the migration of the solvent of at least one active ingredient from one simple matrix to another.

According to one embodiment, the total amount of all the active ingredients is between 0.2 and 50% by weight of the total weight of the molded part taken as a whole.

Advantageously, concerning the monolithic molded part of this invention obtained by multi-shot molding, the interface between the simple matrices welded together, which results in the creation of a connection having good removal resistance between two simple neighboring simple matrices.

By the advantageous association of complementary simple matrices judiciously compatibilized by multi-shot injection, very numerous combinations result which thus make it possible to respond to various problems, in particular in terms of mechanical characteristics such as density, rigidity, permeability, or in terms of aesthetic characteristics such as color, texture, levels of transparency, or even different and/or complementary financial and functional characteristics, in particular by incorporation of active ingredients having different spectra of activity within said materials.

Furthermore, shaping by multi-shot molding makes it possible to obtain geometrically complex shapes of each of the simple matrices, and consequently, of the final molded part, which thus makes it possible to vary the thicknesses of each of the simple matrices and, therefore, to vary the reservoir capacity, the exchange surface and the rate of release of active ingredient from a simple matrix.

According to an alternative embodiment, each of the simple matrices contains an active ingredient different from that contained in the neighboring simple matrix.

According to another alternative embodiment, all the simple matrices can be of different colors.

According to another alternative embodiment, a simple matrix of the molded part is devoid of active ingredient, the latter being intended either to be brought into direct contact with the skin of a human or of an animal, or in a cover layer of at least one active matrix in order to limit the atmospheric diffusion of a volatile active ingredient, in other words, to channel the diffusion of the active ingredient towards the target.

According to one embodiment, each of the simple matrices can come from the same family or from a different thermoplastic polymer family, and that the solvent in which the active ingredients are solubilized can be identical or different in each of the simple matrices; the amount of said solvent can be the same, or different, from one simple matrix to another.

According to one embodiment, each of the simple matrices comes from the same thermoplastic polymer family, and the solvent(s) in which the active ingredient(s) is/are solubilized is/are identical in each of the simple matrices, but the quantity (quantities) of said solvent(s) which has/have enabled the solubilization of the active ingredient(s) is/are different from one simple matrix to another. Different mechanical properties for each of the simple matrices result from the above combinations. It is also known to those skilled in the art that certain active ingredients, in particular essential oils or their components, can be incorporated directly into a polymer matrix without it being necessary to solubilize them in a solvent.

According to one embodiment, each of the simple matrices comes from a family of different thermoplastic polymers, but which are compatible with each other, and the solvent(s) which allowed the solubilization of the active ingredient(s) is/are identical or different from one simple matrix to another, and that the quantity of the solvent(s) is identical or different from one simple matrix to another.

According to one embodiment, the thermoplastic polymers are biodegradable polymers or not, chosen from the group made up of polyolefins and their derivatives, chosen from polyethylenes (PE), polypropylenes (PP), copolymers of ethylene and vinyl acetate (EVA), ether block amides (EBA), polyvinyl chlorides (PVC), polyamides, copolyamides and their derivatives, polyurethanes and their derivatives, styrenics and their derivatives chosen from among the polystyrene-poly(ethylene-butylene)-polystyrenes (SEBS) copolymers, polystyrene-polyisoprene-polystyrene (SIS) copolymers, polystyrene-polybutadiene-polystyrene (SBS) copolymers, vulcanized thermoplastics, agropolymers and their derivatives (polysaccharides, starch, cellulose, proteins), polyesters and their derivatives, as well as the mixture of all these polymers.

According to one embodiment, the active ingredients have biocidal, well-being and cosmetic, therapeutic, phytosanitary and biocontrol effects. The active ingredients are chosen from insecticides, repellents, pheromones, hormones, attractants, perfumes, essential oils, plant extracts, active ingredients with cosmetic effects, pharmaceutical active ingredients, active ingredients with phytosanitary effects. In a known manner, active ingredients having cosmetic effects, pharmaceutical active agents as well as active agents with phytosanitary effects are known to those skilled in the art. Furthermore, in a known manner, an active ingredient can consist of a mixture of essential oils or their compounds, the release profile of the whole of which is compatible with the desired effect.

The insecticides according to this invention can be in viscous liquid or solid form. Insecticides are chosen from the group made up of pyrethroids (ex: permethrin, deltamethrin, cypermethrin, tetramethrin), pyrethrins, carbamates, formamidines (ex: amitraz), carboxylic esters (ex: IR3535), phenylpyrazoles (ex: fipronil), organophosphorus compounds, organohalogenated compounds, neonicotinoids, avermectins and their derivatives, spinosyns, essential oils and their components.

According to one embodiment, the perfumes and hormones are of natural or synthetic origin.

According to a variant of the embodiment, the molded part comprises two simple matrices of thermoplastic polymer, the first matrix containing 0.1 to 50% of its weight of an insecticide belonging to the family of pyrethroids, while the second simple matrix containing 0.1 to 50% of its weight of active ingredient chosen from pyrethrins, carbamates, formamidines, organophosphorus compounds, organohalogenated compounds, neonicotinoids, phenylpyrazoles, avermectins and their derivatives, spinosyns, perfumes, essential oils, pheromones, hormones, active ingredients with cosmetic effects, pharmaceutical active ingredients, active ingredients with phytosanitary effects or a mixture thereof.

According to an alternative embodiment, one of the matrices contains 0.1 to 50% of its weight of insect repellents and that the other matrix contains 0.1 to 50% of its weight of pheromones, of hormones, of attractants, perfumes, essential oils, plant extracts, active ingredients with cosmetic effects, pharmaceutical active ingredients, active ingredients with phytosanitary effects or a mixture thereof. Insect repellents can, in particular, be monoterpene derivatives derived from essential oils, DEET, icaridin and its derivatives, dimethyl phthalate or their mixtures.

In a known manner, the solvent of the active ingredient is chosen from the group of carbonates, esters, alkyls, amines, alcohols, phthalates, plant oils, mineral oils or a mixture thereof.

According to one embodiment, the molded part is in the form of a collar, bracelet, strip, plate, patch, medallion, etc. To treat animal ectoparasites, the molded part is in the form of a collar with a total exchange surface of between 25 and 300 cm² or of a medallion, to be attached to a collar of the animal, the exchange surface of which is between 5 and 100 cm².

Advantageously, for example when the molded part complies with this invention, it incorporates active ingredients with an antiparasitic effect on pets, and this effect is the result of the combination of insecticides specialized in the treatment of ectoparasites, wherein said insecticides each have their different physico-chemical properties (powder, semi-viscous liquid), and opposite diffusion kinetics; the assembly of the different simple matrices containing these allows the diffusion, at the right dose, of these insecticides, throughout the period necessary to achieve long-term efficacy, in the sense that the molded part is capable of repelling the targeted ectoparasites during a period of between a minimum of 6 months and up to 12 months.

The simple matrices constituting the molded part in accordance with this invention may comprise other non-active ingredients, in particular dyes, fillers, stabilizers and other ingredients known to those skilled in the art.

This invention also relates to a method of manufacturing a monolithic molded part made of multiple cohesive matrices for the simultaneous diffusion of volatile active ingredients, of contact ingredients or both, as described above, said complex matrix is formed by the combination of several simple matrices welded together, characterized in that a first homogeneous mixture containing a thermoplastic polymer incorporating a first active ingredient is introduced to constitute the first simple matrix in a first hopper of an injection molding machine and into which is introduced, in parallel, a second homogeneous mixture containing a second thermoplastic polymer incorporating a second active ingredient to constitute the second simple matrix in a second hopper of the same injection molding machine and in which the two simple matrices are put together, each of which contains a different active ingredient, by simultaneous bi-injection of the two homogeneous mixtures.

Advantageously, the mold will have been designed to free up additional cavities at each injection cycle of different polymers.

In one embodiment, each of the simple matrices can come from the same family, or from different families, of thermoplastic polymers, and the solvent in which the active ingredients are solubilized can be identical or different in each of the simple matrices; the amount of said solvent can be the same or different from one simple matrix to another.

In one embodiment of the method, the thermoplastic polymers constituting the first and second simple matrices are different. In such a case, when two neighboring matrices come from families of different polymers, the melting points of said polymers are close to one another, with the difference not to exceed 15° C.

In one embodiment of the method, the thermoplastic polymers constituting the first and second simple matrices are identical.

In a variant embodiment of the method of the invention, three to four independent homogeneous mixtures of polymers are constituted, wherein one of which said mixtures may not contain any active ingredient, in order to constitute the corresponding simple matrices, and wherein the three to four matrices are shaped by simultaneous or sequential multi-shot molding of said mixtures.

In one embodiment of the method, the total amount of all the active ingredients is between 0.2 and 50% by weight of the total weight of the molded part taken as a whole.

EXAMPLE 1

Collar Comprising Active Ingredients Incompatible with Each Other, with Antagonistic Effects The manufacture of an antiparasitic collar (ticks, lice, fleas) that regenerates the skin, intended for a pet, is desired. To do this, the following inputs are available:

essential oils of lemongrass, eucalyptus and *Mentha pulegium* (volatile repellents)

geraniol which, for example, is a component of the essential oil of palmarosa (volatile repellent active)

vitamin F (contact or softening active ingredient or even for regenerating the skin when the collar rubs while wearing)

coconut vegetable oil (emollient, solvent)

EVA granules sold under the EVA PA ALUCIDIA® brand pistachio green dye in granules Protocol for Preparation by Mixing Repellants with Vitamin F:

In a 1 L beaker, 200 g of vitamin F, 160 g of *Mentha pulegium* essential oil, 31.2 g of eucalyptus essential oil, 8 g of lemongrass essential oil and 0.8 g of geraniol are mixed. The mixture is stirred lightly until a homogeneous liquid mixture is obtained.

For all examples, the percentages by weight are related to the total weight of the final matrix.

3519.2 g of EVA are introduced into a cylindrical mixer preheated to 70° C. Then, the above homogeneous liquid mixture is slowly introduced. The mixture is left to be stirred gently until dry granules are obtained. 80 g of pistachio green dye are added and then mixed for 5 minutes. A compound is obtained consisting of EVA polymers loaded with 11.1% by weight of all the active ingredients combined, or 5.5% by weight of vitamin F and 5.6% by weight of repellents.

Shaping by Mono-Injection:

The above compound is injected into a collar 60 cm long by 1 cm wide and weighing 25 g.

The collars (C1) thus obtained were analyzed by GPC assay of the active ingredients contained in the matrix at time zero (T0) after injection, then after 7 days of stability at 50° C. in watertight-sealed packaging. The assay results obtained for the various tracers of repellants are listed in Table 1.

TABLE 1

GPC assay results for collars (C1) containing 5.5% Vitamin F and 5.6% repellents

| | Active ingredient loss (%) | | | | |
|---|---|---|---|---|---|
| Time (days) | Cineole | Citronellal | Pulegone | Citronellol | Geraniol |
| at T0 | 12% | 12% | 11% | 7% | 6% |
| at T = 7 days at 50° C. | 4% | 38% | 10% | 20% | 30% |

At T0, the theoretical amount of geraniol, as well as that of each of the tracers of essential oils, should correspond to the amounts of active repellants initially incorporated into the matrix. Consequently, it is estimated that these quantities represent 100% at T0. However, the GPC assay shows that:
- at T0 after injection, the collar (C1) has already lost 12%, 12%, 11%, 7% and 6% respectively for cineole, citronellal, citronellol and geraniol,
- at T=7 days at 50° C., the loss is accentuated because the collar (C1) has lost 4%, 38%, 10%, 20% and 30% respectively for cineole, citronellal, citronellol and geraniol, or a cumulative loss of 16%, 50%, 21%, 27%, 36% respectively for cineole, citronellal, citronellol and geraniol.

In parallel, by proceeding according to the same protocol, vitamin F was replaced by coconut oil, in the same proportions, then the corresponding collar compound (C2) was injected. The analyses by GPC assay of the collars (C2) gave the results recorded in Table 2.

TABLE 2

GPC assay results for collars (C2) containing 5.5% coconut and 5.6% repellents

| | Active ingredient loss (%) | | | | |
|---|---|---|---|---|---|
| Time (days) | Cineole | Citronellal | Pulegone | Citronellol | Geraniol |
| at T0 | 0% | 0% | 0% | 3% | 0% |
| at T = 7 days at 50° C. | 0% | 3% | 0% | 0% | 0% |

It is observed that:
- at T0 after injection, the collar (C2) retained all the tracers with the exception of citronellol, which shows a loss of 3%,
- at T=7 days at 50° C., only the citronellal has been released (3%)

In conclusion, the mixture of repellants and vitamin F are incompatible with each other when they are incorporated together in this single EVA matrix.

Shaping of the Collars C1 and C2 by Bi-Injection in Compliance with the Invention:

This time, by means of a bi-injection press, the compounds, leading to obtain to collars (C1) and (C2), were injected simultaneously into a mold provided with a bracelet imprint of dimensions identical to that of Example 1. The pistachio green dye was kept to identify the matrix constituting the collar (C1) while a pearly white dye, used in the same proportions as the pistachio green, is used to identify the matrix constituting the collar (C2).

It is observed that the release of repellents is no longer negatively impacted by vitamin F; in addition, it is directly diffused upon contact with the animal's skin to induce its cosmetic effect of softening the skin.

EXAMPLE 2

Bracelet Containing Volatile Active Ingredients with Complementary Effect (Expectoration), but with Staggered Release Limonene (a component of citrus essential oils) is available, as well as *Eucalyptus radiata* essential oil, both of which are known for their expectorant properties.

The protocol for preparing the limonene and eucalyptus essential oil compounds is identical to that of Example 1.

It has been previously observed that the limonene when released first, makes it possible to thin and clear mucus, while the eucalyptus, released second, ensures a persistence of the expectorant activity while promoting decongestion, ideal in stuffy nose and oily cough. The joint action of the two active ingredients thus increases the expulsion of mucus from the trachea or bronchi by sputum or cough.

Studies carried out by the inventors have made it possible to prepare the release profiles of limonene as a function of the polymers used, namely PEBA, EVA and the bio-based polyethylene (PE) copolymer. Compounds loaded with 10% limonene were injected in a bracelet. The different limonene release profiles are shown in FIG. 1.

FIG. 1: release profile at room temperature of limonene incorporated at 10% into different polymer matrices.

It is observed that the polyether block amide (PEBA) bracelet releases limonene very quickly and in a significant quantity when compared to EVA, which releases gradually, and polyethylene which retains. It is noted that for EVA, after 10 days, the remaining amount of limonene is 42%. It is noted that the PEBA bracelet released 70% of the limonene it contained after 2 days, and was empty after 6 days.

10% essential oil of *Eucalyptus radiata* has been incorporated into an EVA polymer matrix. The corresponding release curve is shown in FIG. 2.

Figure 2:
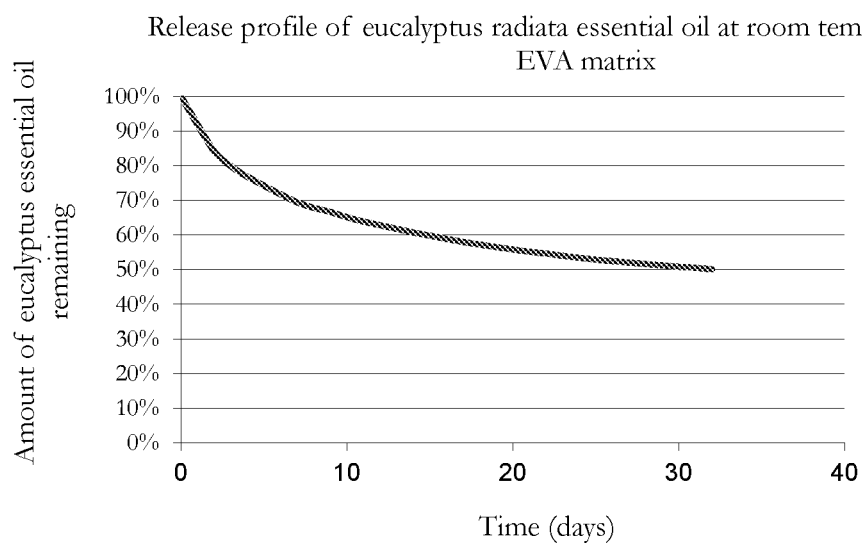

FIG. 2: release profile at room temperature of *Eucalyptus radiata* essential oil incorporated at 10% into an EVA matrix It is observed that the essential oil of *Eucalyptus radiata* is released more gradually, so that the amount remaining after 10 days is still greater than 60%.

Shaping of PEBA and EVA Matrices by Bi-Injection in Accordance with the Invention:

The PEBA polymers loaded with 10% limonene and the EVA polymers loaded with 10% eucalyptus essential oil are shaped into a bracelet by bi-injection as described in Example 1.

Due to its bi-injection shaping, the PEBA matrix rapidly releases limonene and the EVA matrix gradually releases eucalyptus essential oil, each of which makes it possible to achieve the above-mentioned objective, namely the shock effect, followed by a residual effect, the synergy of the two effects inducing expulsion of mucus by sputum or cough.

EXAMPLE 3

Antiparasitic Collar for Animals Comprising Two Synergistic and Complementary Contact Insecticides Having Different Release Profiles Deltamethrin and permethrin are two pyrethroids that are synergistic insecticides (anti-flea and anti-tick). There is also a polyether-based thermoplastic polyurethane (TPU) polymer powder based on polyether (EPAMOULD®), as well as a single solvent which is an ethylhexyl diphenyl phosphate (SANTICIZER 141®).

8% permethrin is solubilized in 22% of SANTICIZER 141® Then, 4% deltamethrin is added, before adding the homogeneous mixture in a single EPAMOULD® matrix. The in vitro release profile of the two insecticides over a period of 16 days is shown in FIG. 2.

Figure 3:
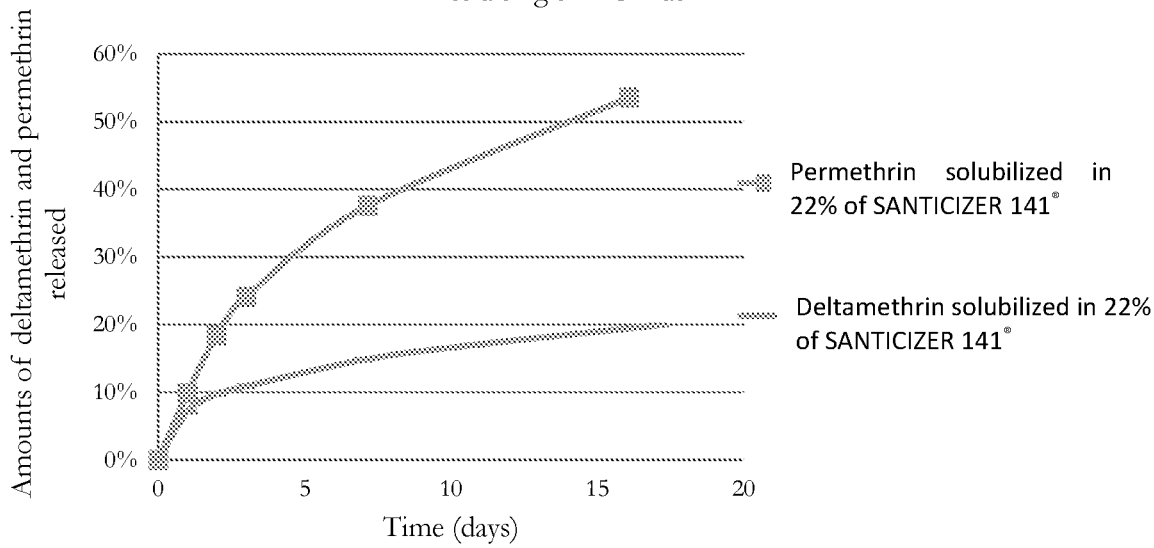

FIG. 3: In vitro release profile in the plant oil from the pest control collar containing 8% permethrin and 4% deltamethrin, both solubilized in 22% SANTICIZER 141®

It is observed that after 15 days, the collar has already released 52% of permethrin, against 18% for deltamethrin. However, to effectively repel fleas, it is preferable that the permethrin be released at doses slightly higher than those of the deltamethrin in FIG. 3. Likewise, to repel ticks effectively, it is desirable that the daily released quantities of deltamethrin be slightly greater than those shown in FIG. 3. The objective is therefore to be able to accelerate the release of deltamethrin, and conversely and simultaneously, to slow down that of permethrin, in order to achieve a substantially similar release profile.

Shaping of Two Simple TPU Matrices by Bi-Injection in Compliance with the Invention:

To achieve the above-mentioned objectives, it seems difficult to obtain a substantially similar release profile of the two insecticides incorporated simultaneously into a single polymer matrix. Therefore, the same amount (8%) of permethrin was solubilized in 5% SANTICIZER® 141 prior to incorporation into a EPAMOULD® matrix as above, in order to obtain a permethrin compound. In parallel, the same quantity of deltamethrin (4%) solubilized in 22% of SANTICIZER® 141 was mixed, prior to incorporation into a EPAMOULD® matrix, in order to obtain a deltamethrin compound.

The two compounds obtained are injected simultaneously in a collar using the bi-injection press as described in Example 1. The in vitro release profile of the two insecticides is shown in FIG. 4.

Figure 4:
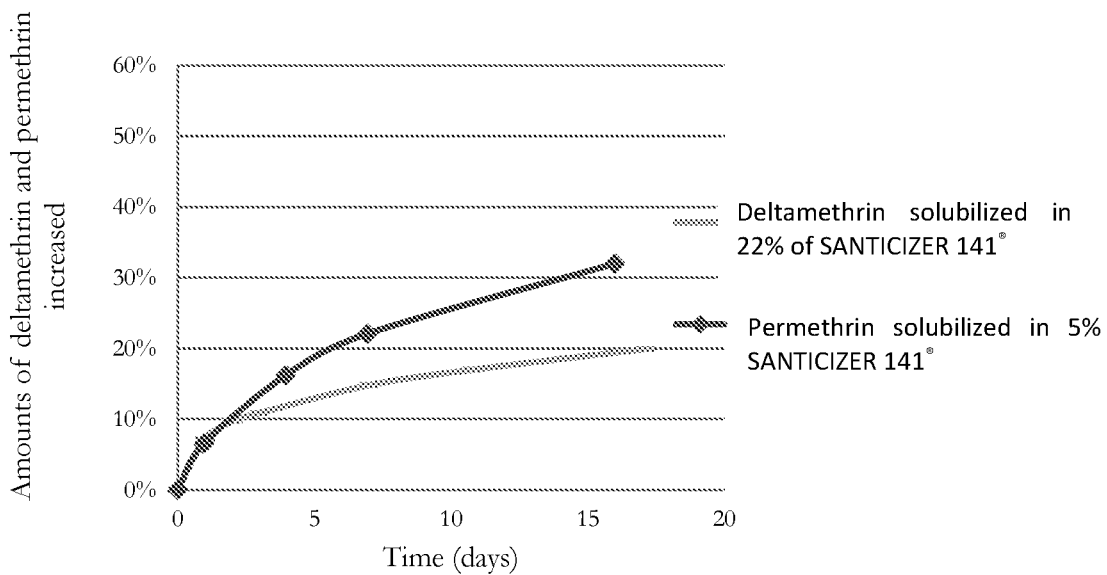

FIG. 4: In vitro release profile in plant oil of the antiparasitic collar obtained by bi-injection including a matrix containing 8% of permethrin solubilized in 5% of SANTICIZER 141® and the other matrix containing 4% of deltamethrin dissolved in 22% of SANTICIZER 141®.

FIG. 4 shows that in order to obtain a substantially similar release profile of the two insecticides, it was necessary that one of the two simple EPAMOULD® matrices incorporate permethrin solubilized at 5%, while the other incorporates deltamethrin solubilized at 22%. The objective that we have set is therefore achieved by shaping the two simple matrices by bi-injection.

The invention claimed is:

1. A monolithic molded part comprised of multiple cohesive matrices, having a non-concentric continuous structure, made up of the combination of two to four simple matrices, welded together and obtained by multi-shot molding, wherein each of said simple matrices is made of thermoplastic polymer and contains a homogeneous mixture of at least one active ingredient and a solvent, said at least one active ingredient being different from another active ingredient contained in a neighboring simple matrix, each of said active ingredient having its own release kinetics, and wherein all of said active ingredients are released simultaneously at substantially different or substantially similar speeds, so that the sum of the quantities of active ingredients released makes it possible to achieve the desired beneficial effects by synergy, wherein said neighboring simple matrices are welded together, side by side or face to face, so that the weld ensures the structural continuity of the monolithic molded part, and wherein said weld, which constitutes the interface between neighboring matrices, consists of the mixture, in molten state, of said thermoplastic polymer forming said matrices, wherein said structural continuity is adapted to the migration of said solvent for said at least one active ingredient from one simple matrix to another, wherein the quantity of solvent is different in each of the simple matrices.

2. The monolithic molded part according to claim 1, wherein each of the simple matrices comes from the same thermoplastic polymer family or each of the simple matrices comes from a family of different thermoplastic polymers.

3. The monolithic molded part according to claim 2, wherein the solvent where the active ingredients are solubilized, is identical from one simple matrix to another or is different from one simple matrix to another.

4. The monolithic molded part according to claim 1, wherein the quantity of solvent in one of the simple matrices is greater than that of a neighboring matrix.

5. The monolithic molded part according to claim 1, wherein the thermoplastic polymers are biodegradable polymers or not, chosen from the group consisting of polyolefins and their derivatives chosen from polyethylenes (PE), polypropylenes (PP), copolymers of ethylene and vinyl acetate (EVA), ether block amides (EBA), polyvinyl chlorides (PVC), polyamides, copolyamides and their derivatives, polyurethanes and their derivatives, styrenics and their derivatives chosen from among the polystyrene-poly (ethylene-butylene)-polystyrenes (SEBS) copolymers, polystyrene-polyisoprene-polystyrene (SIS) copolymers, polystyrene-polybutadiene-polystyrene (SBS) copolymers, vulcanized thermoplastics, agropolymers and their derivatives chosen from polysaccharides, starch, cellulose and proteins, polyesters and their derivatives, as well as the mixture of all these polymers.

6. The monolithic molded part according to claim 1, wherein the active ingredients have biocidal effects, well-being effects, cosmetic effects, therapeutic effects, phytosanitary effects and biocontrol effects.

7. The monolithic molded part according to claim 6, wherein the active ingredients are chosen from insecticides, repellents, pheromones, hormones, attractants, perfumes, essential oils, plant extracts, and pharmaceutical active ingredients.

8. The monolithic molded part according to claim 7, wherein the insecticides are chosen from the group consisting of pyrethroids, pyrethrins, carbamates, formamidines, carboxylic esters, phenylpyrazoles, organophosphorus compounds, organohalogenated compounds, neonicotinoids, avermectins and their derivatives, spinosyn, essential oils and their components.

9. The monolithic molded part according to claim 1, wherein itthe monolithic molded part comprises two simple matrices in thermoplastic polymer, the first matrix containing 0.1 to 50% of its weight in an insecticide belonging to the family of pyrethroids while the second simple matrix containing 0.1 to 50% of its weight in active ingredient chosen from pyrethrins, carbamates, formamidines, organophosphorus compounds, organohalogenated compounds, neonicotinoids, phenylpyrazoles, avermectins and their derivatives, spinosyns, perfumes, essential oils, pheromones, hormones, active ingredients with cosmetic effect, pharmaceutical active ingredients, active ingredients with phytosanitary effects or a mixture thereof.

10. The monolithic molded part according to claim 1, wherein one of the simple matrices contains 0.1 to 50% of its weight in repellent, and at least one of the other simple matrices contains 0.1 to 50% of its weight in pheromone, hormone, attractant, perfumes, essential oil, plant extract, active ingredient with cosmetic effect, pharmaceutical active ingredient, active ingredient with phytosanitary effect, or a mixture thereof.

11. The monolithic molded part according to claim 1, wherein the monolithic molded part is in the form of a collar, a bracelet, a strap, a plate, a patch, or a medallion.

12. A method for manufacturing a monolithic molded part comprised of multiple cohesive matrices according to claim 1, for the simultaneous diffusion, of volatile active ingredients, by contact ingredients or both, wherein said monolithic molded part is made up of the combination of two to four simple matrices welded together, wherein at least a first homogeneous mixture containing a thermoplastic polymer incorporating a first active ingredient and a first solvent which enables the active ingredients to solubilize is introduced into a first hopper of an injection molding machine to constitute a first simple matrix, and wherein at least a second homogenous mixture, containing a second thermoplastic polymer which incorporates a second active ingredient and a second solvent which enables the active ingredients to solubilize is introduced simultaneously into a second hopper of the same injection molding machine to constitute a second simple matrix, and wherein the first and second simple matrices, each of which contains a different active ingredient and a different quantity of solvent, are shaped simultaneously by bi-injection of the at least first and second homogeneous mixtures.

13. The method according to claim 12, wherein each of the simple matrices is obtained from the same thermoplastic polymer family.

14. The method according to claim 12, wherein each of the simple matrices comes from a different thermoplastic polymer family.

15. The method according to claim 13, wherein a solvent where the active ingredients are solubilized is identical or is different from one simple matrix to another.

16. The method according to claim 14, wherein a solvent where the active ingredients are solubilized is identical or is different from one simple matrix to another.

17. The method according to claim 15, wherein the quantity of the solvent in one of the simple matrices is greater than that of a neighboring matrix.

18. The method according to claim 16, wherein the quantity of the solvent in one of the simple matrices is greater than that of a neighboring matrix.

19. The method according to claim 14, wherein the melting point of two neighboring matrices results from families of different polymers, and wherein the melting points differentials of said different polymers do not exceed 15° C.

* * * * *